US009880114B2

(12) United States Patent
Ju et al.

(10) Patent No.: US 9,880,114 B2
(45) Date of Patent: Jan. 30, 2018

(54) INDUSTRIAL CT SCANNING TEST SYSTEM AND FLUID PRESSURE LOADING APPARATUS

(71) Applicant: CHINA UNIVERSITY OF MINING AND TECHNOLOGY, BEIJING, Beijing (CN)

(72) Inventors: Yang Ju, Beijing (CN); Jianqiang Wang, Beijing (CN); Ruidong Peng, Beijing (CN); Lingtao Mao, Beijing (CN); Hongbin Liu, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 15/539,811

(22) PCT Filed: Jul. 5, 2016

(86) PCT No.: PCT/CN2016/088558
§ 371 (c)(1),
(2) Date: Jun. 26, 2017

(87) PCT Pub. No.: WO2017/012466
PCT Pub. Date: Jan. 26, 2017

(65) Prior Publication Data
US 2017/0350832 A1   Dec. 7, 2017

(30) Foreign Application Priority Data
Jul. 21, 2015   (CN) .......................... 2015 1 0432189

(51) Int. Cl.
*A61B 6/00*   (2006.01)
*G01N 23/04*  (2006.01)

(52) U.S. Cl.
CPC ...... *G01N 23/046* (2013.01); *G01N 2223/311* (2013.01); *G01N 2223/33* (2013.01); *G01N 2223/40* (2013.01)

(58) Field of Classification Search
CPC ............ G01N 23/046; G01N 2223/33; G01N 2223/40; G01N 2223/311
See application file for complete search history.

(56) References Cited

U.S. PATENT DOCUMENTS

2016/0216218 A1*   7/2016   Grader ................. G01N 23/046

FOREIGN PATENT DOCUMENTS

| CN | 2924518 Y | 7/2007 |
|---|---|---|
| CN | 102042989 A | 5/2011 |

(Continued)

OTHER PUBLICATIONS

International Search Report for PCT/CN2016/088558, dated Sep. 21, 2016, ISA/CN.

*Primary Examiner* — Courtney Thomas
(74) *Attorney, Agent, or Firm* — U.S. Fairsky LLP; Yue Xu

(57) ABSTRACT

A fluid pressure loading device applied to an industrial computed tomography scanning test system includes a body, a sample accommodating chamber and at least one fluid medium chamber being provided in the body. Each of the at least one fluid medium chamber is provided therein with a piston, the corresponding fluid medium chamber is separated into two chambers by the piston, one of the two chambers is in communication with an external hydraulic medium via oil lines provided in the body, the other of the two chambers is in communication with the sample accommodating chamber, and one end, facing towards the sample accommodating chamber, of the piston is extendable into the sample accommodating chamber. With the loading device, real-time loading of a test sample can be realized, thus (Continued)

improving a simulation accuracy of the system, and multi-directional loading of the sample can be realized.

20 Claims, 8 Drawing Sheets

(56) References Cited

FOREIGN PATENT DOCUMENTS

| | | | |
|---|---|---|---|
| CN | 102809574 | A | 12/2012 |
| CN | 102967611 | A | 3/2013 |
| WO | 2004019029 | A1 | 3/2004 |

* cited by examiner

INDUSTRIAL CT SCANNING TEST SYSTEM AND FLUID PRESSURE LOADING APPARATUS

The present application is the national phase of International Application No. PCT/CN2016/088558, titled "INDUSTRIAL CT SCANNING TEST SYSTEM AND FLUID PRESSURE LOADING APPARATUS", filed on Jul. 5, 2016 which claims the priority to Chinese Patent Application No. 201510432189.6, titled "INDUSTRIAL COMPUTED TOMOGRAPHY SCANNING TEST SYSTEM AND FLUID PRESSURE LOADING DEVICE", filed on Jul. 21, 2015, with the State Intellectual Property Office of the People's Republic of China, the entire disclosures of which applications are incorporated herein by reference.

FIELD

This application relates to the technical field of sample scanning, and particularly to an industrial computed tomography scanning test system and a fluid pressure loading device.

BACKGROUND

Industrial computed tomography (CT) scanning technique provides an effective laboratory technique for the analysis and study of internal structures of materials and is widely used in various related fields.

A conventional industrial CT generally uses X-rays to penetrate a section of an object, and performs a rotational scan, to reconstruct an image of the internal part of the object by means of a high-performance computer system. The principle is described as follows. The intensity of X-rays after penetrating the object to be detected is measured by a specific detector, and in the meantime, a scanning action among the X-ray machine, the detector and the object to be detected is performed, thus obtaining complete data required for reconstructing a CT image, and finally, the image of the section of the object is reconstructed by using these data based on a certain algorithm.

However, due to essential characteristics of the industrial CT scanning technique, to obtain a better resolution, in one aspect, the size of a focus of the ray beam is required to be reduced as much as possible, to restrict the penetrating ability of the rays; and in another aspect, the size of the sample should be carefully restricted and a stable rotation of the sample during the scanning should be guaranteed, to restrict the dimension of an object to be scanned. These restrictions adversely affect the application of the CT technique in mechanics analysis to a great extent. A loading device is indispensable in mechanics experiments; however, a conventional loading device generally has a large volume and weight, and is hence difficult to be directly placed in the industrial CT machine to be used in the scanning process. Therefore, in the conventional technology, loading is generally performed outside of the CT machine, and then the loaded sample is placed on a test-bed of the CT. This loading method has a low accuracy, and once the loading is finished, the load applied on the test sample is not adjustable.

For homogeneous materials such as metal, rubber, and ceramic, a small sample and a miniature loading device may be used for the scan and analysis, which may ensure that rays are able to penetrate the sample to form an image, and the image can meet the requirement for a certain resolution ratio. However, for the analysis of the mechanical loading performed on a geotechnical material, the following challenges should be overcome. Firstly, the sample cannot be too small; otherwise, the analysis may be influenced by a dimensional effect such that a desired experimental result cannot be obtained. However, the increase in the size of the sample may inevitably result in the increase in the size of the loading device, thus causing a series of issues such as, rays are difficult to penetrate the sample, the loading tonnage is increased, and the resolution ratio of the image is decreased. Secondly, loading schemes are generally complicated; to simulate a stress state of the geotechnical material in practical engineering, a simple uniaxial tensile and compression experiment is not sufficient, various complicated loading experiments are further required, such as multi-axial compression experiment, percolation experiment, and hydraulic fracturing experiment. Also, sometimes loading and unloading procedures are required to be performed many times. Hence, a higher requirement is imposed on the implementation and control of the loading device.

Therefore, a technical issue to be addressed by those skilled in the art is to provide an industrial CT scanning test system, which can realize multi-directional loading on a sample, to meet test requirements

SUMMARY

An object of the present application is to provide an industrial CT scanning test system and a fluid pressure loading device. With the loading device, real-time loading of a test sample can be realized, thus improving a simulation accuracy of the system, and multi-directional loading of the sample can be realized, thus meeting test requirements.

In order to solve the above technical issues, a fluid pressure loading device applied to the industrial CT scanning test system is provided according to the present application. The fluid pressure loading device includes a body, and a sample accommodating chamber and at least one fluid medium chamber are provided in the body. Each of the at least one fluid medium chamber is provided therein with a piston, and the piston separates the corresponding fluid medium chamber into two chambers, one chamber is in communication with an external hydraulic medium via oil lines provided in the body, the other chamber is in communication with the sample accommodating chamber, and one end, facing towards the sample accommodating chamber, of the piston is extendable into the sample accommodating chamber;

the at least one fluid medium chamber specifically includes a first fluid medium chamber and a second fluid medium chamber, and correspondingly, the pistons are specifically a first piston and a second piston, the first piston is placed inside the first fluid medium chamber, the second piston is placed inside the second fluid medium chamber, and an axial direction of the first piston is arranged to be perpendicular to an axial direction of the second piston; and an auxiliary hole is provided in the body at a position opposite to the fluid medium chamber, the auxiliary hole has a radial dimension smaller than a radial dimension of the fluid medium chamber, and a plug matching with the auxiliary hole is further provided.

Since the sample is placed in the body, the fluid pressure loading device has a compact structure and a small volume, which facilitates the placement thereof on a sample scanning stage. Also, a real-time adjustment of the force applied on the sample is realized by controlling a flow quantity of a fluid flowing into the fluid medium chamber, thus further improving the efficiency of the test.

Optionally, the at least one fluid medium chamber further includes a third fluid medium chamber, a third piston is provided inside the third fluid medium chamber, and an axial direction of the third piston, the axial direction of the second piston and the axial direction of the first piston constitute a three-axis coordinate system.

Optionally, in the axial direction of the piston, a cross sectional dimension of a first end surface of the piston is greater than a cross sectional dimension of a second end surface of the piston, the first end surface is an end surface towards the end of the fluid medium chamber, and the second end surface is an end face towards the end of the sample accommodating chamber.

Optionally, in a longitudinal cross section of the body, a wall thickness, at a side where the fluid medium chamber is arranged, of the body is greater than a wall thickness, at a side opposite to the side where the fluid medium chamber is arranged, of the body.

Optionally, the body is further provided with a passage configured to communicate a lower surface of the body with the sample accommodating chamber, to facilitatedisposing a sample into the sample accommodating chamber via the passage, and a plug is provided in an inlet of the passage.

Optionally, oil ports configured to be in communication with an external fluid medium source are all arranged in an upper end face of the body, and the oil ports are in communication with the corresponding fluid medium chambers via internal oil passages.

Optionally, the fluid pressure loading device further includes two connection heads, an upper end and a lower end of the body are each provided with a flange, and the two connection heads are connected to the flanges at the two ends of the body via bolts.

Further, an industrial CT scanning test system is further provided according to the present application, which includes a test base, a multi-axis motion turntable supported on the test base, a ray generating device, an image acquisition device, one or multiple fluid pressure loading device, and a control device;

the industrial CT scanning test system further includes at least one fluid pressure loading device, the fluid pressure loading device is the fluid pressure loading device in the above descriptions, and when a scanning test is performed, each fluid pressure loading device is placed on a sample platform of the multi-axis motion turntable, and loading of loads in different directions is performed on the sample in real-time according to test requirements.

Since the industrial CT scanning test system has the above fluid pressure loading device, it also has the above technical effects of the fluid pressure loading device.

BRIEF DESCRIPTION OF THE DRAWINGS

For more clearly illustrating embodiments of the present application or the technical solution in the conventional technology, drawings referred to describe the embodiments or the conventional technology will be briefly described hereinafter. Apparently, the drawings in the following description are only several embodiments of the present application, and for the person skilled in the art other drawings may be obtained based on these drawings without any creative efforts.

Figure 1:
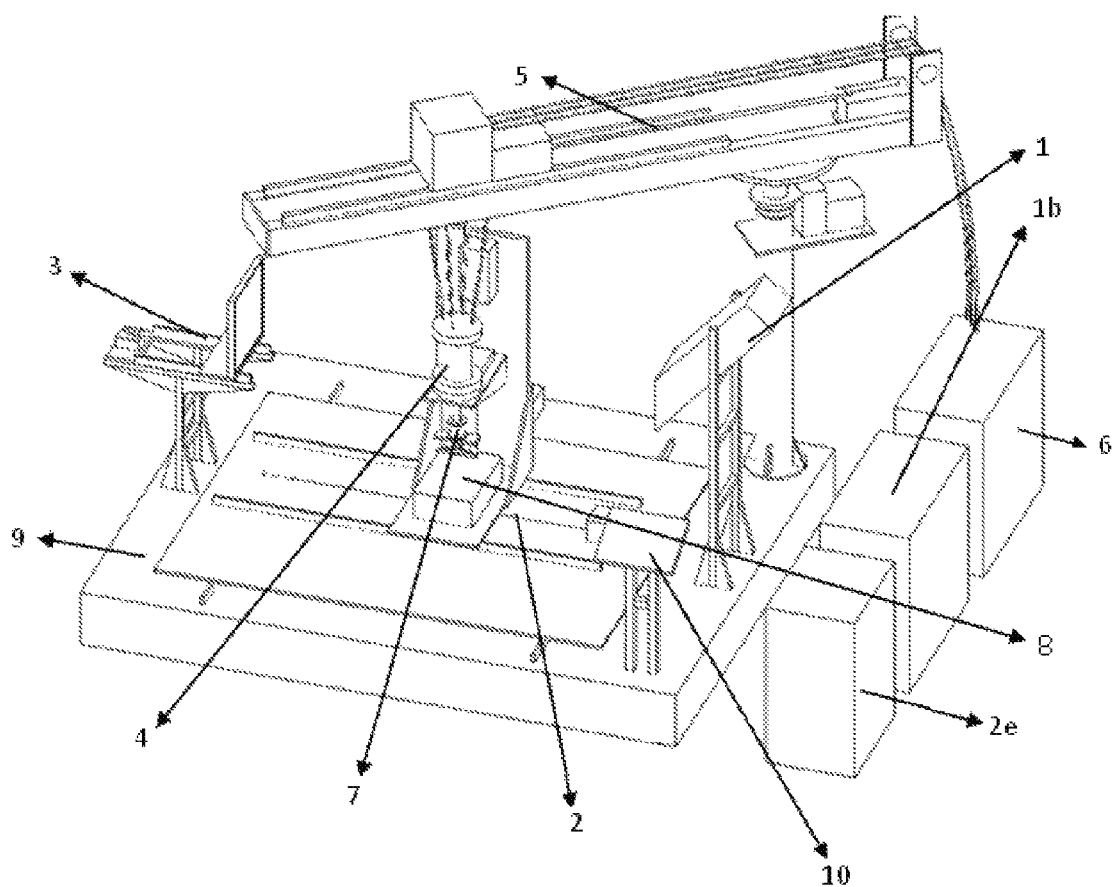
FIG. 1 is a schematic view showing the structure of an industrial CT scanning test system according to an embodiment of the present application.

Corresponding relationships between names of components in FIGS. 1 to 8 and reference numerals are as follows:

| 1 ray generating device, | 1b high pressure generator, |
|---|---|
| 2 multi-axis motion turntable, | 2e control cabinet |
| 3 image acquisition device, | 4 fluid pressure loading device, |
| 41 body, | 42 first piston, |
| 43 first flange, | 44 second flange, |
| 45 second connection head, | 45a connection hole, |
| 46 first connection head, | 47 second piston, |
| 4a sample accommodating chamber, | 4b fluid medium chamber, |
| 4c auxiliary hole, | 4d fluid medium chamber, |
| 4e passage, | 5 synchronous rotary device, |
| 5a multi-passage synchronous high pressure rotator, | |
| 5b cantilevered holder, | 5c rotatable holder, |
| 5d fixing holder, | 5b1 transverse beam, |
| 5b2 end plate, | 5b3 third support plate, |
| 5b4 guide rail, | 5b5 slider, |
| 5b6 lead screw, | 5b7 nut seat, |
| 5b10 upright plate, | 5b11 bearing, |
| 5b12 circular tube, | 5d1 upright column, |
| 5d2 bottom plate, | 5d3 rib plate, |
| 5d4 horizontal support plate, | 5d5 rib plate, |
| 5d7 motor, | 5c1 central column, |
| 5c2 second support plate, | 5c3 rib plate, |
| 5c4 gear, | 5c5 bearing, |
| 5c6 bearing, | 6 control device, |
| 7 automatic winder, | 7a threaded rod, |
| 7b nut, | 7c sliding plate, |
| 7d bobbin, | 7e bearing, |
| 7f guide rod, | 7g coupling plate, |
| 8 pressure-strain acquisition device, | 9 test base, |
| 10 control panel. | |

DETAILED DESCRIPTION

An object of the present application is to provide an industrial CT scanning test system and a fluid pressure loading device. The loading device can realize real-time loading of a test sample and improve a simulation accuracy of the system, and also may realize multi-directional loading of the sample, thus meeting the test requirements.

For those skilled in the art to better understand technical solutions of the present application, the present application is described in detail in conjunction with drawings and embodiments hereinafter.

Reference is made to FIG. 1, which is a schematic view showing the structure of an industrial CT scanning test system according to an embodiment of the present application.

An industrial CT scanning test system is provided according to the present application. This system includes a test base 9, a multi-axis motion turntable 2 supported on the test base 9, a ray generating device 1, an image acquisition device 3, a fluid pressure loading device 4 and a control device 6. The multi-axis motion turntable 2 is provided with a sample platform configured to place a sample thereon. The sample platform may be rotated or moved in a predetermined direction with respect to the test base 9 according to test requirements. The predetermined direction here may be a direction along a principal ray beam, i.e., a front-rear direction, may also be a direction perpendicular to the principal ray beam in a horizontal plane, i.e., a right-left direction, and may also be a direction perpendicular to the principal ray beam in a vertical plane, i.e., an up-down direction. Similarly, the sample platform may rotate about a vertical direction. Generally, in order to achieve the above rotating function and the above various linear motion functions, multiple sample platforms may be provided, and the sample platforms may specifically include a rotatable sample platform, a stage movable in the front-rear direction, a stage movable in the right-left direction and a stage movable in the up-down direction. Each of the sample platforms may be driven by a motor to move, and the motor is connected to the control device 6 via control lines (power supply lines and signal lines). An operator controls the motors by operating the control device 6, thus corresponding motions of sample platforms are realized.

At present, the rays emitted by the ray generating device 1 are generally X-rays. Of course other types of rays may also be adopted. Herein, the technical solution is introduced by taking X-rays as an example. The ray generating device 1 may include a ray tube, a high pressure generator 1*b* and a control cabinet 2*e*. Since X-ray is radioactive, the ray generating device 1 is generally placed inside a shield room. The ray tube is connected to the high pressure generator 1*b* and the control cabinet via high voltage cables and control lines. The control cabinet is connected to the control device 6 via network cables. The control device 6 can adjust a voltage and a current at which the rays are generated and other parameters, and can perform machine training and calibration. In consideration of safety of a tester, a beam emitting control switch of the X-ray control cabinet is connected to a lead door trigger of the shield room and an indicator lamp, to ensure that the indicator lamp is on when rays are emitted and no rays may be emitted when the lead door is open.

The image acquisition device 3 is arranged at a side opposite to the ray generating device 1, and is configured to acquire rays emitted by the ray generating device 1 and perform imaging of the sample based on the acquired rays. The image acquisition device 3 may include a flat panel detector and a movable platform. The flat panel detector is fixed on the movable platform. The movable platform is movable with respect to the test base 9 in an emitting direction of the principal ray beam to achieve imaging with different magnifying powers. The movable platform may be driven to move by a motor, and of course may be driven to move by other components as well.

The movable platform may be manufactured with an aluminium alloy profile. The movable platform includes two upright columns, a transverse beam, a rib plate, etc., as long as a reliable support to the flat panel detector can be realized. The movement of the movable platform may be realized by the cooperation of a guide rail and a slider. The flat panel detector may be purchased according to the required model, and parameters such as an effective area, a number of picture elements and gray scale may be selected according to the demand.

It is to be noted that, the ray detector in the image acquisition device 3 is not limited to the above flat panel detector, and may also be other types of detectors, as long as the above function can be achieved.

The fluid pressure loading device 4 completes real-time loading of loads in different directions on the sample according to the test requirements. When a scanning experiment is performed, the fluid pressure loading device and the sample are placed together on the sample platform of the multi-axis motion turntable 2. The fluid may be a liquid, such as a hydraulic oil or water, and may also be a gas. The fluid pressure loading device 4 may include at least one loading cylinder through which the loading of the pressure on the sample is realized.

The sample mentioned in this specification may be a geotechnical sample and may also be other types of samples. Herein, the technical effects of the test system provided according to the present application are specifically described taken the geotechnical sample to be tested as an example herein.

In the industrial CT scanning test system provided herein, the fluid pressure loading device 4 is employed, a dead weight of the loading device is reduced as much as possible, and a large loading force may be provided, thus the requirements for deformation and destructive tests of most geotechnical materials may be met. Also, the loading cylinder of the loading device and the sample are placed together on the sample platform of the multi-axis motion turntable 2 and are scanned together by the rays, and a loading force applied on the geotechnical sample by the loading cylinder may be adjusted in real time according to the test requirements, thus improving an efficiency of the test.

Furthermore, loading forces in different directions on the sample may be achieved according to the number of the loading cylinders provided. For example, the loading forces in two directions on the sample may be realized by providing two loading cylinders. The loading forces in three different directions on the sample may be realized by providing three loading cylinders, for example, a simulation experiment in which the forces in three-axis coordinate system are loaded may be implemented.

Figure 2:
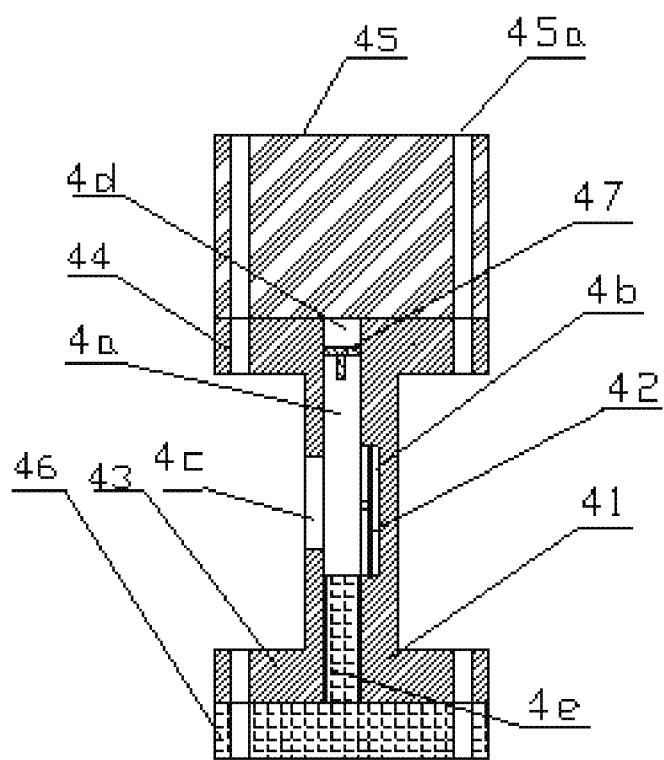
FIG. 2 is a schematic view showing the structure of a fluid pressure loading device according to a specific embodiment of the present application.
Figure 3:
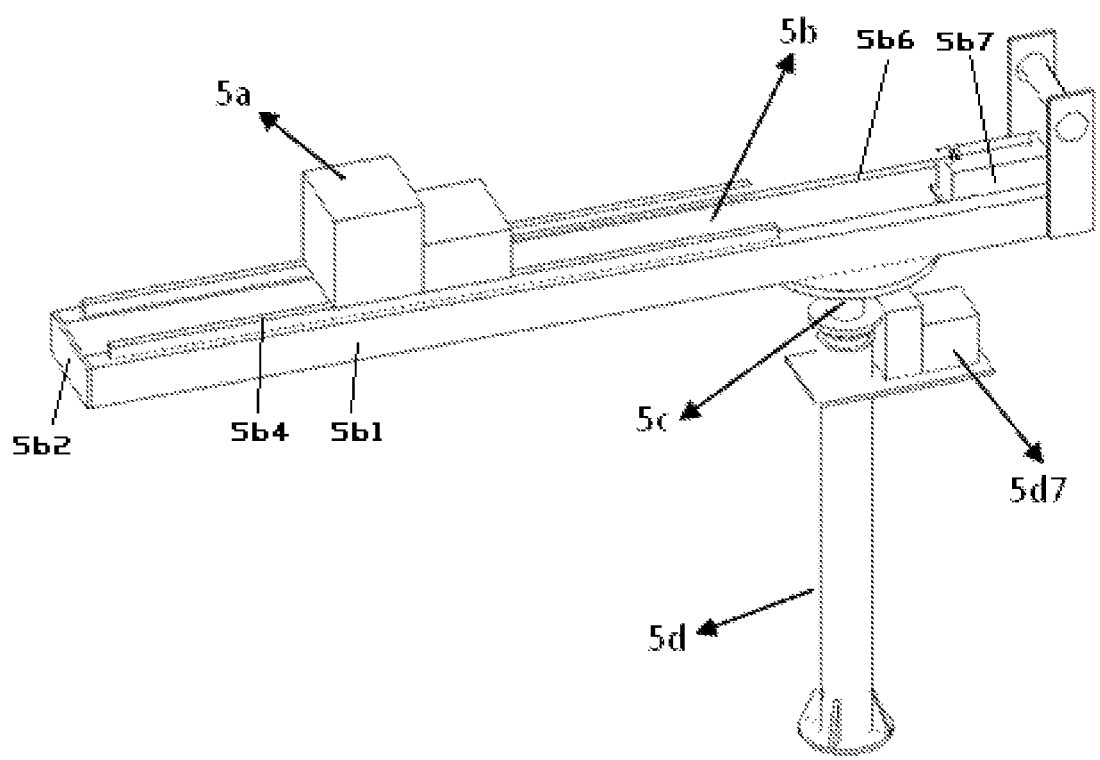
FIG. 3 is a schematic view showing the structure of a synchronous rotary device according to an embodiment of the present application.

Reference is made to FIG. 2, which is a schematic view showing the structure of a fluid pressure loading device in a specific embodiment of the present application. Only two loading directions, i.e., a vertical direction and a horizontal direction, are shown in FIG. 2.

Specifically, in a specific embodiment, the fluid pressure loading device 4 includes a body 41, and a sample accommodating chamber 4*a* and at least one fluid medium chamber are provided in the body 41. The sample accommodating chamber 4*a* is configured to accommodate and fix the sample. Each of the at least one fluid medium chamber is provided therein with a piston, and the piston separates a corresponding fluid medium chamber into two chambers, one chamber is in communication with an external hydraulic medium via oil lines provided in the body 41, and the other chamber is in communication with the sample accommodating chamber 4*a*. One end, facing toward the sample accommodating chamber 4*a*, of each piston is extendable into the sample accommodating chamber 4*a*. The fluid medium chamber and the piston form a loading cylinder.

In this embodiment, when a sample is performed with a force loading, firstly the sample is placed inside the body 41 of the loading device, and then an external medium source is activated to fill a fluid medium into the fluid medium chamber in the body 41. Under the pushing of the fluid medium flowing into the fluid medium chamber, the piston placed inside the fluid medium chamber is moved toward the sample accommodating chamber 4a, and with the fluid medium being continually filled, the piston abuts against the sample and applies a certain force on the sample. The operator may calculate the force applied on the sample based on a pressure of the fluid medium in a pipeline and an area of the piston, thereby realizing the loading of force on the sample.

In the fluid pressure loading device in the above embodiment, the sample is placed in the body, thus the fluid pressure loading device has a compact structure and a small volume, which may be conveniently placed on a sample scanning stage. Also, a real-time adjustment of the force applied on the sample is realized by controlling a flow quantity of the fluid flowing into the fluid medium chamber, thus further improving the efficiency of the test.

The force loading manner provides pressures in different directions by an embedded loading cylinder, the pressure may reach 200 MPa by taking a liquid medium as an example, and three-axis, two-axis and single-axis loading tests may be performed. The structure of the loading device is simple and the volume thereof may be designed to match the samples.

The body 41 may be manufactured with an aluminium alloy material having a high strength and a light weight. Thus, the strength requirement for the body 41 under the condition of loading with a large load is met as well as the requirement for the ray to penetrate when CT scan is performed is met. Also, the dead weight of the body is reduced to meet the restriction requirement of the turntable for the weight of a piece to be scanned.

In the case that the forces applied on the sample are two-dimensional forces in two directions perpendicular to each other (two-axis forces), correspondingly, the number of the fluid medium chambers is two, and the two fluid medium chambers are respectively a first fluid medium chamber 4b and a second fluid medium chamber 4d. Correspondingly, the pistons are specifically a first piston 42 and a second piston 47. The first piston 42 is placed inside the first fluid medium chamber 4b and the second piston 47 is placed inside the second fluid medium chamber 4d, and also, an axial direction of the first piston 42 and an axial direction of the second piston 47 are arranged to be perpendicular to each other. Herein, the axial direction of the first piston 42 is in the horizontal direction and the axial direction of the second piston 47 is in the vertical direction. Of course, the axial directions of the first piston 42 and the second piston 47 may be arranged according to requirements of practical loading forces.

When three-axis forces are simulated, the fluid medium chambers further include a third fluid medium chamber, and a third piston is provided inside the third fluid medium chamber. An axial direction of the third piston, the axial direction of the second piston and the axial direction of the first piston constitute a three-axis coordinate system. Although the schematic view of the third fluid medium chamber is not provided herein, those skilled in the art may easily understand and implement this technical solution according to the text description provided herein.

Further, in order to use a small internal pressure of the loading cylinder to obtain a large loading force on the sample, the piston may be designed to have a variable cross section, i.e., a cross sectional dimension of a first end surface of the piston is greater than a cross sectional dimension of a second end surface of the piston. The first end surface is an end surface towards the end of the fluid medium, and the second end surface is an end surface towards the end of the sample accommodating chamber 4a.

In practical tests, a working pressure inside the loading cylinder is relatively small, and pressures for oil pipe connection and a pump are easily satisfied, the pressure loaded on the sample is large to facilitate achieving a large loading force, and especially for a direction of Z-axis (the vertical direction), the part in this direction may not interfere with penetrating of the rays, thus this part has no special requirements for the dimension.

In addition, for the loading in two directions of X-axis and Y-axis, on the premise that a magnitude of the loading forces is ensured, the adverse effects caused by the rays on the sample when the rays penetrate the sample should be reduced as much as possible. Therefore, the body 41 should have a sufficiently small overall dimension, at the same time an experimental load thereof should also be ensured. Thus, in processing process, the body 41 is processed to apply loads in an asymmetric manner, i.e., in a longitudinal cross section of the body 41, a wall thickness, at a side where the fluid medium chamber is provided, of the body 41 is greater than a wall thickness, at a side opposite to the side where the fluid medium chamber is provided, of the body 41. As indicated from FIG. 2 that, a thickness, at a side where the first fluid medium chamber 4b is provided, of the body 41 is greater than the thickness, at a side opposite to the side where the first fluid medium chamber 4b is provided, of the body 41.

In addition, an auxiliary hole 4c is further provided in the body 41 at a position opposite to the fluid medium chamber, and the auxiliary hole 4c has a radial dimension smaller than a radial dimension of the fluid medium chamber, and providing the auxiliary hole 4c may reduce the difficulty in processing of the fluid medium chamber. Of course, in the case that a force loading experiment is performed, the auxiliary hole 4c needs to be blocked by a plug.

In addition, for ensuring a processing accuracy of an inner wall of the fluid medium chamber, and for avoiding the loading oil lines to interfere with the rays, oil ports configured to be in communication with the external liquid medium are all arranged in an upper end surface of the body 41, and the oil ports are in communication with the fluid medium chambers via internal passages respectively. The oil ways are directly processed in the body, thus may avoid the interference to the rays caused by externally connected oil pipelines.

For easily arranging the sample inside the sample accommodating chamber 4a from outside, the body 41 is further provided with a passage 4e configured to communicate a lower surface of the body 41 with the sample accommodating chamber 4a, in order that the sample may be easily disposed into the sample accommodating chamber 4a via the passage 4e. And also, an inlet end of the passage 4e is provided with a plug.

For facilitating mounting and assembling of the body 41, an upper end and a lower end of the body 41 may each be provided with a flange, and connection heads are connected to the flanges at two ends of the body 41 via bolts. At the lower end, a first flange 43 and a first connection head 46 are cooperatively connected, and at the upper end, the second flange 44 and the second connection head 45 are cooperatively connected. The connection heads and the flanges may be provided with connection holes, and the bolts pass through the connection holes of the connection heads and the flanges and are fixed to matched nuts respectively, thus achieving the connection between the connection heads and the flanges. FIG. 2 shows a connection hole 45a in the second connection head 45.

In addition, for ensuring sealing between the piston and the fluid medium chamber, a sealing component may further be provided between the piston and the fluid medium chamber. The sealing component may be a sealing ring, a mounting groove is processed in a circumferential wall of the piston, and the sealing ring is disposed inside the mounting groove.

The sample platform according to the above embodiments is movable or rotatable with respect to the test base 9, that is to say, the body 41 according to the above embodiments may also move with respect to the test base 9 during testing. Therefore, for avoiding the pipelines of the external oil line in communication with the body 41 to generate interference, the following arrangement may further be performed.

Figure 4:
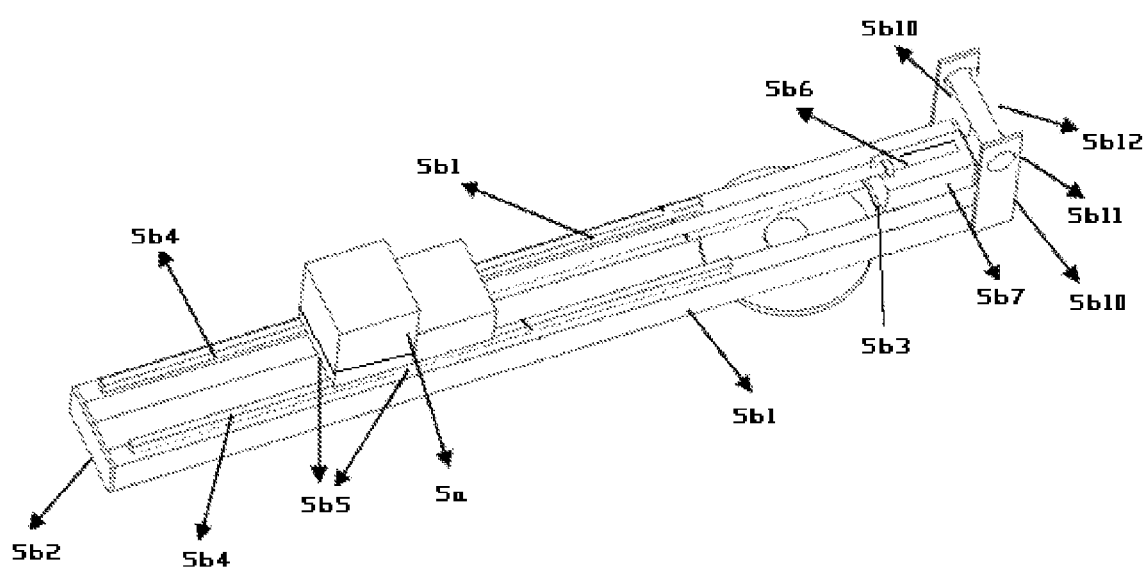
FIG. 4 is a schematic view showing the structure of a cantilevered holder.
Figure 5:
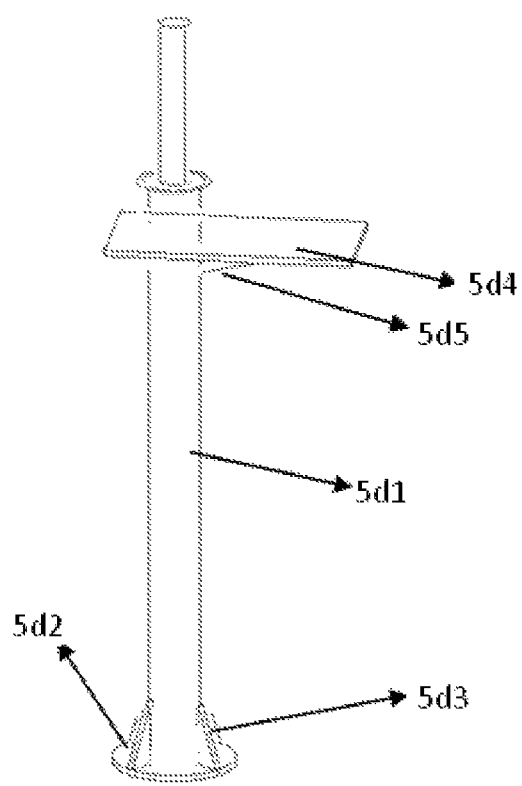
FIG. 5 is a schematic view showing the structure of a fixing holder.
Figure 6:
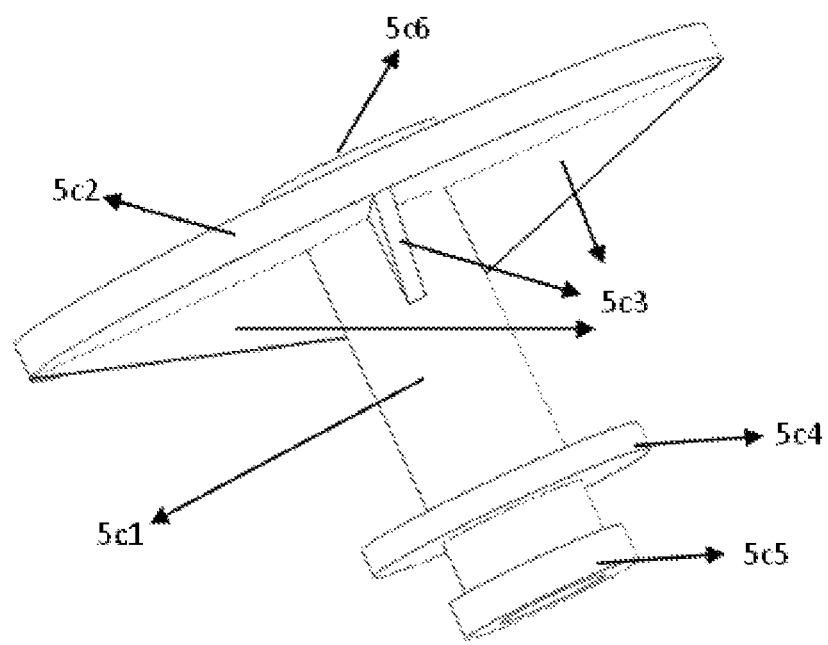
FIG. 6 is a schematic view showing the structure of a rotatable holder.
Figure 7:
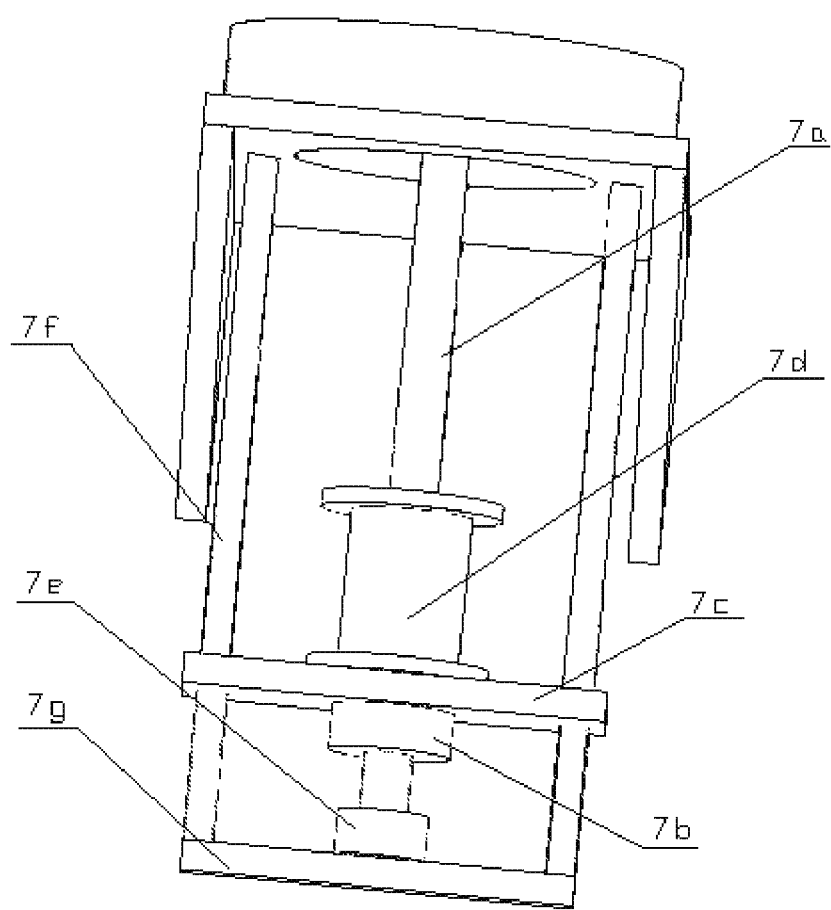
FIG. 7 is a schematic view showing the structure of an automatic winder according to an embodiment of the present application.
Figure 8:
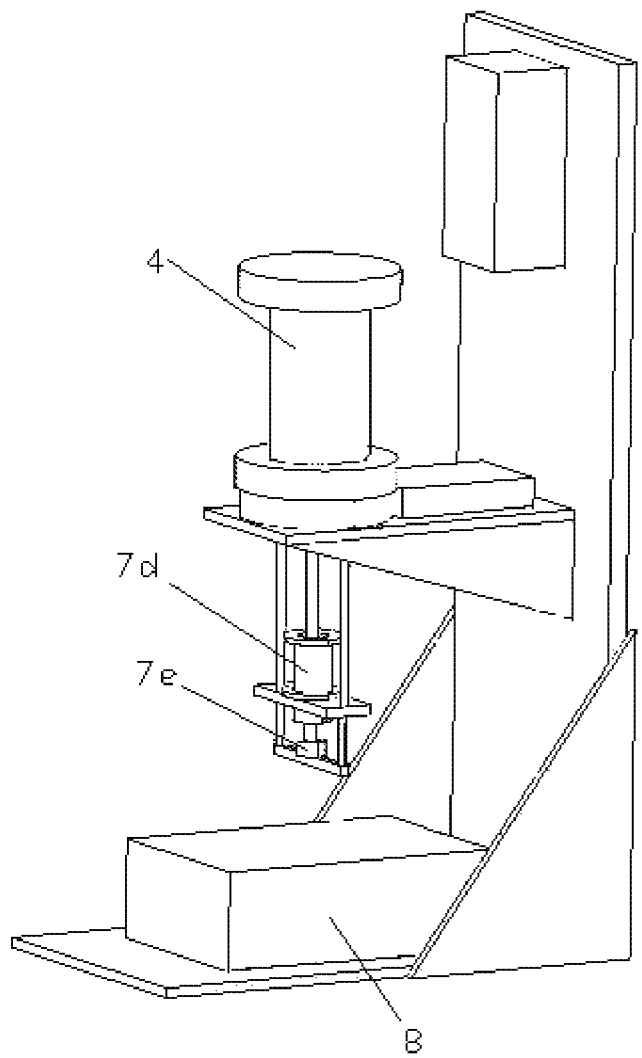
FIG. 8 is a schematic view showing the assembly of the automatic winder and a sample platform.

Reference is made to FIGS. 3 to 6, FIG. 3 is a schematic view showing the structure of a synchronous rotary device according to an embodiment of the present application; FIG. 4 is a schematic view showing the structure of a cantilevered holder; FIG. 5 is a schematic view showing the structure of a fixing holder; and FIG. 6 is a schematic view showing the structure of a rotatable holder.

The industrial CT scanning test system according to the above embodiments may further be provided with a synchronous rotary device 5, and the synchronous rotary device 5 includes a fixing holder 5d and a cantilevered holder 5b. The cantilevered holder 5b is disposed over the loading cylinder, a lower end of the fixing holder 5d is supported on the test base 9, and the cantilevered holder 5b is vertically rotatably connected to an upper end of the fixing holder 5d, i.e., the cantilevered holder 5b is rotatable with respect to the fixing holder 5d in the vertical direction.

The cantilevered holder 5b is provided with a guide rail 5b4, a slider 5b5 cooperating with the guide rail 5b4, and a driving component configured to drive the slider 5b5 to move along the guide rail 5b4. Positions of the medium pipelines configured to be in communication with the loading cylinder are limited by the slider 5b5, to allow the medium pipelines to slide with respect to the guide rail 5b4 along with the slider 5b5, and extend downward from the position of the slider 5b5 to connect the loading cylinder located on the sample platform. The control device 6 may control the driving component to move, to allow the slider 5b5 to be always located right above the loading cylinder, i.e., the slider 5b5 may move synchronously with the loading cylinder. In this way, the position of the slider 5b5 may be adjusted in real time according to different sized samples and different positions of the sample platform in case of different magnifying powers, to allow the medium pipelines to be always perpendicular to the loading cylinder, thus avoiding winding of the pipelines on the loading cylinder and ensuring the normal operation of the loading cylinder.

The synchronous rotary device 5 may further include a multi-passage high pressure rotator 5a fixedly connected to the slider 5b5. The multi-passage high pressure rotator 5a specifically includes a fixed end pipe joint and a rotatable end pipe joint which are in communication with each other via internal passages. The fixed end pipe joint is in communication with a driving source via an oil pipe, and the rotatable end pipe joint is in communication with the loading cylinder. The rotatable end pipe joint is synchronously rotatable together with the rotation of the sample platform and may not impede the rotation of the loading cylinder.

In the above various embodiments, the driving component in the synchronous rotary device 5 may include a motor, a lead screw 5b6, and a nut seat 5b7 cooperating with a threaded end of the lead screw 5b6. The threaded end of the lead screw 5b6 is arranged in an inner threaded hole of the nut seat 5b7, and another end of the lead screw 5b6 is fixedly connected to the slider 5b5. The motor drives the lead screw 5b6 to rotate, thus achieving the reciprocating movement of the slider 5b5 under the driving of the lead screw 5b6.

Specifically, the synchronous rotary device 5 in the above embodiments may further include a rotatable holder 5bc arranged between the fixing holder 5d and the cantilevered holder 5b. The fixing holder 5d includes an upright column 5d1, a bottom of the upright column 5d1 is supported on the test base 9, and a horizontal support plate 5d4 is provided at an upper end of the upright column 5d1. For increasing the reliability of connection, a rib plate 5d5 may further be provided between the horizontal support plate 5d4 and the upright column 5d1, and a bottom plate 5d2 may be provided at a lower end of the upright column 5d1, and a rib plate 5d3 is additionally provided between the bottom plate 5d2 and the upright column 5d1.

The rotatable holder includes a central column 5c1, and a lower end of the central column 5c1 is sleeved on the upper end of the upright column 5d1 and is circumferentially rotatably connected to the upper end of the upright column 5d1 via a bearing 5c5. A gear 5c4 is further fixed on the central column 5c1, and a motor 5d7 configured to drive the gear to rotate is further provided. The motor 5d7 is fixed to the horizontal support plate 5d4, and the motor 5d7 drives the central column 5c1 to rotate with respect to the upright column 5d1 via the gear 5c4. A second support plate 5c2 is fixed to an upper end of the central column 5c1, and the cantilevered holder is fixed to the second support plate 5c2.

For ensuring the reliability of fixing of the second support plate 5c2 to the central column, a rib plate 5c3 may further be additionally provided between the central column and the second support plate 5c2, and also for increasing the rotation flexibility of the central column 5c1, the upper end of the central column 5c1 may also be additionally provided with a positioning bearing 5c6.

The cantilevered holder includes two transverse beams 5b1 extending horizontally, and an end plate 5b2 and a third support plate 5b3 respectively connected to two ends of the two transverse beams 5b1. The driving component is arranged above the third support plate 5b3, the third support plate 5b3 is rotatably connected to the fixing holder 5d, and the guide rail 5b4 is arranged on upper surfaces of the two transverse beams 5b1.

The rear ends of the transverse beams 5b1 are further provided with two parallel upright plates 5b10, and a circular tube 5b12 is further connected between the two parallel upright plates 5b10. The circular tube 5b12 is rotatably connected to the two parallel upright plates 5b10 via bearings 5b11 respectively. The pipelines are rested on a surface of the circular tube 5b12, and in the case that the slider slides forward and backward, the pipelines may roll together with the circular tube 5b12, to reduce the friction between the pipelines and the circular tube.

For accurately obtaining loading forces applied on the sample by the loading cylinders, a pressure-strain acquisition device 8 may be further provided on the test base 9, to acquire pressure-strain parameters of the sample in various directions. The control device 6 controls the pressure of the fluid medium in the fluid pressure loading device 4 according to the pressure-strain parameters. Specifically, the stress-strain acquisition device 8 includes a sensor and a signal acquisition apparatus. The sensor is arranged on the body, the signal acquisition apparatus is generally arranged on the test base 9 right below the sample platform, and the signal acquisition apparatus and the sensor are connected via signal lines and the like. For avoiding winding of the signal lines during rotation of the sample platform, the following arrangements are adopted by the present application, which are specifically described as follow.

The industrial CT scanning test system in the above embodiments may further include an automatic winder 7 arranged below the sample platform. The automatic winder 7 includes a threaded rod 7*a*, a nut assembly and a bobbin 7*d*. An upper end of the threaded rod 7*a* is fixedly connected to the sample platform, and a lower end of the threaded rod 7*a* passes through a threading hole of the multi-axis motion turntable 2 to extend downward. The nut assembly includes a nut 7*b* and a positioning component configured to limit a circumferential position of the nut 7*b* with respect to a fixing frame of the multi-axis motion turntable 2. The nut 7*b* is arranged on an outer threaded portion of the threaded rod 7*a*, the bobbin 7*d* is sleeved on the threaded rod 7*a*, the bobbin 7*d* is axially movably connected to the threaded rod 7*a*, and the bobbin 7*d* is fixedly connected to the nut 7*b*.

During the installation, firstly, signal lines in the loading device on the sample platform are wound around a surface of the bobbin 7*d*, to allow the signal lines to be transferred to other connection components after the signal lines are wound on the surface of the bobbin 7*d*. In this way, when the sample platform rotates, the threaded rod 7*a* also rotates synchronously with the sample platform. And since the nut 7*b* is circumferentially fixed, the nut 7*b* moves upward or downward with respect to the threaded rod 7*a*, and the bobbin 7*d* fixed to the nut 7*b* also moves upward or downward along with the nut 7*b*. In this way, the signal lines transferred from an edge through hole of the rotatable sample platform also rotate along with the turntable, and thus also rotates about the bobbin 7*d*. The signal lines rotate and move upward and downward with respect to the bobbin 7*d* and form a spiral movement, thus the signal lines are automatically wound around the surface of the bobbin 7*d*, thereby preventing the signal lines from being knotted to adversely affect the rotation of the loading device during the rotation of the sample platform.

In a specific embodiment, the positioning component may be guide rods 7*f* respectively located at two sides of the threaded rod 7*a* and a sliding plate 7*c* which is sleeved on the two guide rods 7*f* and slidably connected to the guide rods 7*f*, and the nut 7*b* is fixed to the sliding plate 7*c*. Such a structure is simple, and facilitates the arrangement of the nut 7*b*.

Further, a coupling plate 7*g* is further provided at a tail end of the two guide rods 7*f*, and the coupling plate 7*g* is provided with a bearing 7*e*. A free end of the threaded rod 7*a* is connected to the coupling plate 7*g* via the bearing 7*e*. In this structure, a position of the free end of the threaded rod 7*a* is also relatively limited, which facilitates the rotating stability of the threaded rod 7*a*.

Of course, the shield room may be further provided therein with a control panel 10. With the control panel 10, the parameters of the loading device may be set and the load loaded on the sample may be displayed by a touch screen interface of the control panel 10, thus facilitates performing the loading on the sample. The specific structure of the control panel may refer to the conventional apparatus, which is not described here in detail.

It is to be noted that, terms indicating directions and positions herein, such as "upper", "lower", are defined by reference of the positional relationship between the various components in FIGS. 1 to 8, and are only intended to clarify description of the technical solutions, thus should not be regarded as a limitation to the protection scope of the present application.

The industrial CT scanning test system and the fluid pressure loading device according to the present application are described in detail hereinbefore. The principle and the embodiments of the present application are illustrated herein by specific examples. The above description of the examples is only intended to help the understanding of the idea of the present application. It should be noted that, for the person skilled in the art, a few of modifications and improvements may be made to the present application without departing from the principle of the present application, and these modifications and improvements are also deemed to fall into the scope of the present application defined by the claims.

What is claimed is:

1. A fluid pressure loading device applied to an industrial computed tomography scanning test system, comprising a body, a sample accommodating chamber and at least one fluid medium chamber being provided in the body, wherein:
    each of the at least one fluid medium chamber is provided therein with a piston, the corresponding fluid medium chamber is separated into two chambers by the piston, one of the two chambers is in communication with an external hydraulic medium via oil lines provided in the body, the other of the two chambers is in communication with the sample accommodating chamber, and one end, facing towards the sample accommodating chamber, of the piston is extendable into the sample accommodating chamber;
    the at least one fluid medium chamber comprises a first fluid medium chamber and a second fluid medium chamber, the corresponding pistons are a first piston and a second piston respectively, the first piston is arranged inside the first fluid medium chamber, the second piston is arranged inside the second fluid medium chamber, and an axial direction of the first piston is configured to be perpendicular to an axial direction of the second piston; and
    an auxiliary hole is provided in the body at a position opposite to the fluid medium chamber, the auxiliary hole has a radial dimension smaller than a radial dimension of the fluid medium chamber, and a plug matching with the auxiliary hole is further provided.

2. The fluid pressure loading device according to claim 1, wherein the at least one fluid medium chamber further comprises a third fluid medium chamber, a third piston is provided inside the third fluid medium chamber, and an axial direction of the third piston, the axial direction of the second piston, and the axial direction of the first piston constitute a three-axis coordinate system.

3. The fluid pressure loading device according to claim 1, wherein in the axial direction of each of the pistons, a cross sectional dimension of a first end surface, of each of the pistons is greater than a cross sectional dimension of a second end surface, of each of the pistons, the first end surface is an end surface towards the end of the fluid medium chamber, and the second end face is an end surface towards the end of the sample accommodating chamber.

4. The fluid pressure loading device according to claim 1, wherein in a longitudinal cross section of the body, a wall thickness, at a side where the fluid medium chamber is arranged, of the body is greater than a wall thickness, at a side opposite to the side where the fluid medium chamber is arranged, of the body.

5. The fluid pressure loading device according to claim 1, wherein the body is further provided with a passage configured to communicate a lower surface of the body with the sample accommodating chamber, configured to easily dispose a sample into the sample accommodating chamber via the passage, and a plug is provided in an inlet of the passage.

6. The fluid pressure loading device according to claim 1, wherein oil ports configured to be in communication with an external fluid medium source are all arranged in an upper end surface of the body, and the oil ports are in communication with corresponding fluid medium chambers via internal oil passages.

7. The fluid pressure loading device according to claim 1, further comprising two connection heads, wherein an upper end and a lower end of the body are each provided with a flange, and the two connection heads are connected to the flanges at the two ends of the body via bolts.

8. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 1, and when a scanning test is performed, each fluid pressure loading device is placed on a sample platform of the multi-axis motion turntable, and loading of loads in different directions are performed to a sample in real-time according to test requirements.

9. The fluid pressure loading device according to claim 2, wherein the body is further provided with a passage configured to communicate a lower surface of the body with the sample accommodating chamber, configured to easily dispose a sample into the sample accommodating chamber via the passage, and a plug is provided in an inlet of the passage.

10. The fluid pressure loading device according to claim 3, wherein the body is further provided with a passage configured to communicate a lower surface of the body with the sample accommodating chamber, configured to easily dispose a sample into the sample accommodating chamber via the passage, and a plug is provided in an inlet of the passage.

11. The fluid pressure loading device according to claim 2, wherein oil ports configured to be in communication with an external fluid medium source are all arranged in an upper end surface of the body, and the oil ports are in communication with corresponding fluid medium chambers via internal oil passages.

12. The fluid pressure loading device according to claim 3, wherein oil ports configured to be in communication with an external fluid medium source are all arranged in an upper end surface of the body, and the oil ports are in communication with corresponding fluid medium chambers via internal oil passages.

13. The fluid pressure loading device according to claim 2, further comprising two connection heads, wherein an upper end and a lower end of the body are each provided with a flange, and the two connection heads are connected to the flanges at the two ends of the body via bolts.

14. The fluid pressure loading device according to claim 3, further comprising two connection heads, wherein an upper end and a lower end of the body are each provided with a flange, and the two connection heads are connected to the flanges at the two ends of the body via bolts.

15. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 2, and when a scanning test is performed, each fluid pressure loading device is placed on a sample platform of the multi-axis motion turntable, and loading of loads in different directions are performed to a sample in real-time according to test requirements.

16. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 3, and when a scanning test is performed, each fluid pressure loading device is placed on a sample platform of the multi-axis motion turntable, and loading of loads in different directions are performed to a sample in real-time according to test requirements.

17. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 4, and when a scanning test is performed, each fluid pressure loading device is placed on a sample platform of the multi-axis motion turntable, and loading of loads in different directions are performed to a sample in real-time according to test requirements.

18. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 5, and when a scanning test is performed, each fluid pressure loading device is placed on a sample platform of the multi-axis motion turntable, and loading of loads in different directions are performed to a sample in real-time according to test requirements.

19. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 6, and when a scanning test is performed, each fluid pressure loading device is placed on a sample platform of the multi-axis motion turntable, and loading of loads in different directions are performed to a sample in real-time according to test requirements.

20. An industrial computed tomography scanning test system, comprising a test base, a multi-axis motion turntable supported on the test base, a ray generating device, an image acquisition device, a fluid pressure loading device and a control device, wherein
the fluid pressure loading device is the fluid pressure loading device according to claim 7, and when a scanning test is performed, each fluid pressure loading device is placed on a sample platform of the multi-axis motion turntable, and loading of loads in different directions are performed to a sample in real-time according to test requirements.

* * * * *